United States Patent
Kruzic

(10) Patent No.: US 6,405,596 B1
(45) Date of Patent: Jun. 18, 2002

(54) ULTRASONIC AUSTENITIC WELD SEAM INSPECTION METHOD AND APPARATUS

(75) Inventor: Ronald W. Kruzic, Spring, TX (US)

(73) Assignee: Chicago Bridge & Iron Company, Plainfield, IL (US)

( * ) Notice: Subject to any disclaimer, the term of this patent is extended or adjusted under 35 U.S.C. 154(b) by 0 days.

(21) Appl. No.: 09/688,304

(22) Filed: Oct. 13, 2000

(51) Int. Cl.[7] .............................................. G01N 29/04
(52) U.S. Cl. ........................... 73/611; 73/1.82; 73/1.86
(58) Field of Search ................... 73/1.82, 1.86, 73/611

(56) References Cited

U.S. PATENT DOCUMENTS

| | | | | |
|---|---|---|---|---|
| 3,791,199 A | * | 2/1974 | Toth et al. ...................... | 73/609 |
| 3,873,830 A | * | 3/1975 | Forster ......................... | 250/236 |
| 4,106,326 A | * | 8/1978 | Lather et al. ................. | 73/1.86 |
| 4,173,139 A | * | 11/1979 | Conn .......................... | 73/1.84 |
| 4,182,155 A | * | 1/1980 | Fowler ........................ | 73/1.81 |
| 4,660,419 A | * | 4/1987 | Derkacs et al. ............... | 73/622 |
| 5,214,616 A | * | 5/1993 | Terhune et al. ............... | 367/99 |
| 5,404,755 A | * | 4/1995 | Olson et al. .................. | 73/639 |
| 5,537,876 A | * | 7/1996 | Davidson et al. ............. | 73/624 |
| 5,677,490 A | * | 10/1997 | Gunther et al. ............... | 73/622 |
| 6,138,495 A | * | 10/2000 | Paltieli et al. ............... | 73/1.86 |

* cited by examiner

Primary Examiner—Hezron Williams
Assistant Examiner—Jacques Saint Surin
(74) Attorney, Agent, or Firm—Marshall, Gerstein, & Borun.

(57) ABSTRACT

An array of dual-element transducers for automated, ultrasonic inspection of a weld seam in austenitic material is configured through the use of a schematic representation of the weld seam. The weld is divided into zones, and separate transducers are selected to inspect each zone. A creep-wave transducer is used to inspect the uppermost zone, and an L-wave transducer is used to inspect a lower zone. The L-wave transducer is connect to a computer processor to serve "double-duty": it is used with one set of gate and gain settings to process direct reflections of the emitted sound, and with another set of gate and gain settings to process indirect, mode-converted reflections of the sound. Gate settings are determined by measuring sound path distances from the schematic. Test plates are used to determine sensitivity settings, and to confirm adequate width of field for each transducer.

17 Claims, 6 Drawing Sheets

ULTRASONIC AUSTENITIC WELD SEAM INSPECTION METHOD AND APPARATUS

BACKGROUND OF THE INVENTION

This invention relates to the inspection of weld seams, and more particularly to the ultrasonic inspection of weld seams in structures.

In structures, it is common for structural plates to be joined by welded seams. The welds can be made not only with ordinary ferritic steel, but also with metal that is high in nickel content. Ordinary ferritic steel weld material solidifies in a relatively uniform structure. Weld metal that is high in nickel content, however, solidifies in a face-centered cubic (austenitic) crystal structure that typically has an elongated (dendritic) grain structure.

It has been previously known that ultrasonic testing (UT) can be used to inspect ordinary ferritic steel welds for defects. Arrays of single-element transducers have been mounted on rolling carts that travel along a ferritic steel weld (commonly pipeline girth welds). The transducers are tied to computerized data collection systems that allow quick inspection of the seams.

Unfortunately, however, the dendritic structure of austenitic welds make them much more difficult to inspect by ultrasonic testing. The elongated grains of the structure tend to refract the ultrasonic signals, creating a high level of noise in the collected data. Consequently, the use of UT inspection of austenitic welds has been limited.

It has been found that dual-element, longitudinal-wave transducers can be used to provide useful inspection of austenitic welds. However, unlike single-element, shear-wave transducers, dual-element transducers focus on a particular distance, and do not provide information about as broad an area as covered by a single-element transducer. Consequently, linear scanning of austenitic welds has been limited to situations where the operator is interested in focusing on only a particular part of a weld, such as the fusion line between the weld metal and the base metal.

Where the operator is interested in inspecting the full volume of the weld, a "mastering" process is conventionally used. In such a process, the operator probes for defects throughout the thickness of a weld by manual sliding a transducer towards and then away from the weld. Moving the transducer laterally with respect to the weld is necessary to redirect the sound from the transducer through different sections of the weld. Rastering is a slow and awkward process. It appears that some efforts have been made to mount dual-element transducers on carriages for automated UT inspection. However, determining the transducer arrays that provide reliable results has been difficult.

Consequently, where the full volume of an austenitic weld must be inspected, those skilled in the art have generally chosen to forego the problems of ultrasonic inspection and rely instead upon radiographic inspection. Tanks for the storage of cryogenic liquids such as liquefied natural gas, for example, are field-constructed from plates joined by austenitic butt welds that require 100% inspection for weld defects. Such welds have been conventionally inspected with photographic film exposed by dangerous levels of radiation. Such radiographic inspection is a potential safety hazard and a time-consuming step that sometimes controls the erection schedule of such tanks.

SUMMARY OF THE INVENTION

A new method for easily configuring a useful array of dual-element transducers for automated ultrasonic inspection of austenitic weld seams has been developed. The new arrays facilitate ultrasonic inspection of austenitic weld seams, making it an attractive alternative to radiographic inspection.

It has been found that a useful array of transducers can be readily configured by using a schematic of a section of the weld to be screened. Transducer positions and sound paths are laid out on the schematic, and it is then divided into at least two inspection zones. Transducer housing size and sound paths are selected for each inspection zone, and the maximum and minimum sound path distances from the transducer positions to the boundaries of the heat-affected zones are measured. Focal spot distances are selected that provide adequate sensitivity at both the minimum and the maximum sound path distances. Transducer standoff distances and gate settings are established from the schematic. Test plates are then used to determine transducer gain settings and to confirm adequate width-of-field. The transducers are then mounted on a carriage and used to inspect a test weld seam. It is particularly useful to select a creep wave transducer to inspect the upper portion of the weld metal and heat-affected zones, and to select two sets of gain and gate settings for another transducer, one set of settings for obtaining and analyzing direct reflections of sound from that transducer and the other set of settings for obtaining and analyzing indirect reflections of that sound. To do this, the processor is programmed to analyze the signals from that transducer as though they were signals from two separate transducers.

Applying the standards used in the non-destructive test profession, these methods and apparatus have been found to be capable of reliably detecting both machined flaws and flaws produced by intentional welding errors in austenitic welds.

BRIEF DESCRIPTION OF THE DRAWINGS

The invention may be better understood by referring to the accompanying drawings, in which.

DETAILED DESCRIPTION

Figure 1:
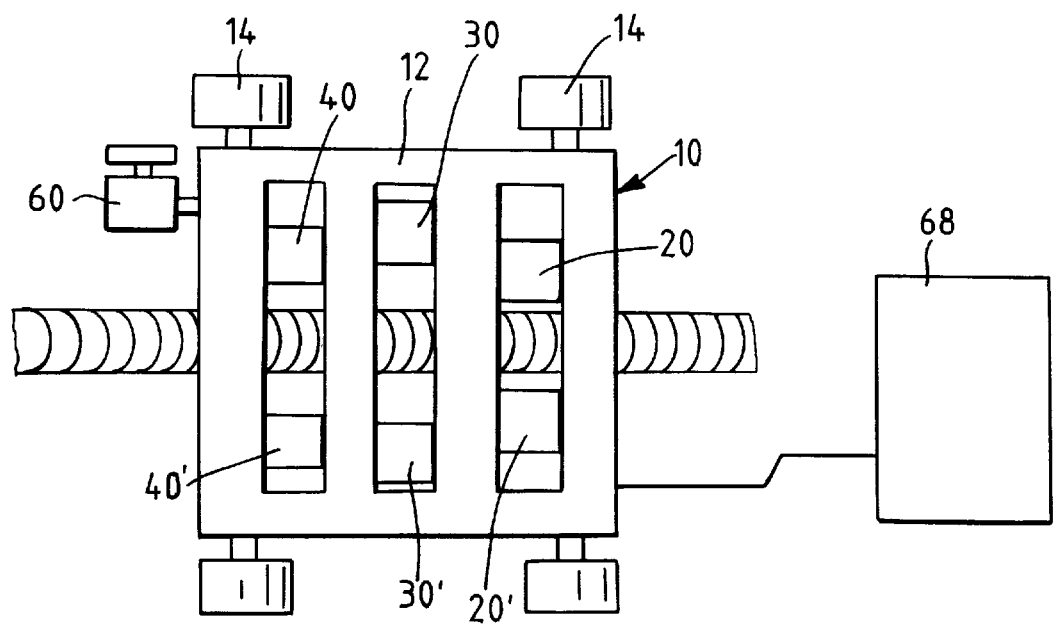
FIG. 1 is a plan view of a carriage configured in accordance with the present invention.
Figure 2:
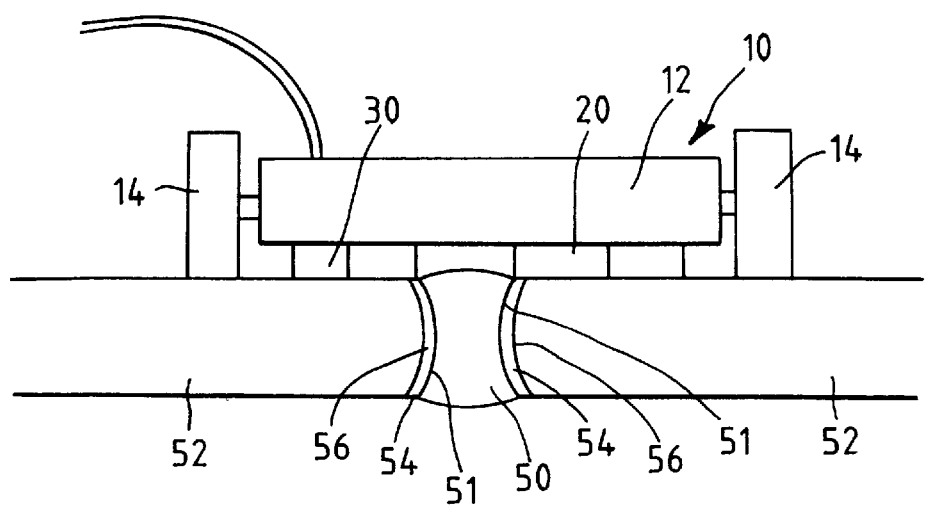
FIG. 2 is a sectional view of the carriage of FIG. 1 being used to inspect a weld seam.

FIGS. 1 and 2 illustrate one embodiment of a carriage 10 that can be effectively used for automated, ultrasonic inspection of an austenitic weld seam. The carriage that has been illustrated includes a frame 12, magnetic wheels 14, and a creep wave transducer 20, an intermediate-zone transducer 30, and a lower-zone transducer 40.

In use, the carriage rides over the length of a weld seam, as seen in FIG. 2. As illustrated, the weld seam is greater than 16 mm thick, and includes weld metal 50 that joins a pair of plates 52. Each plate includes a heat-affected zone 54 that extends from a fusion line 51 between the weld metal and the plates to a boundary 56 within the plate.

Figure 3:
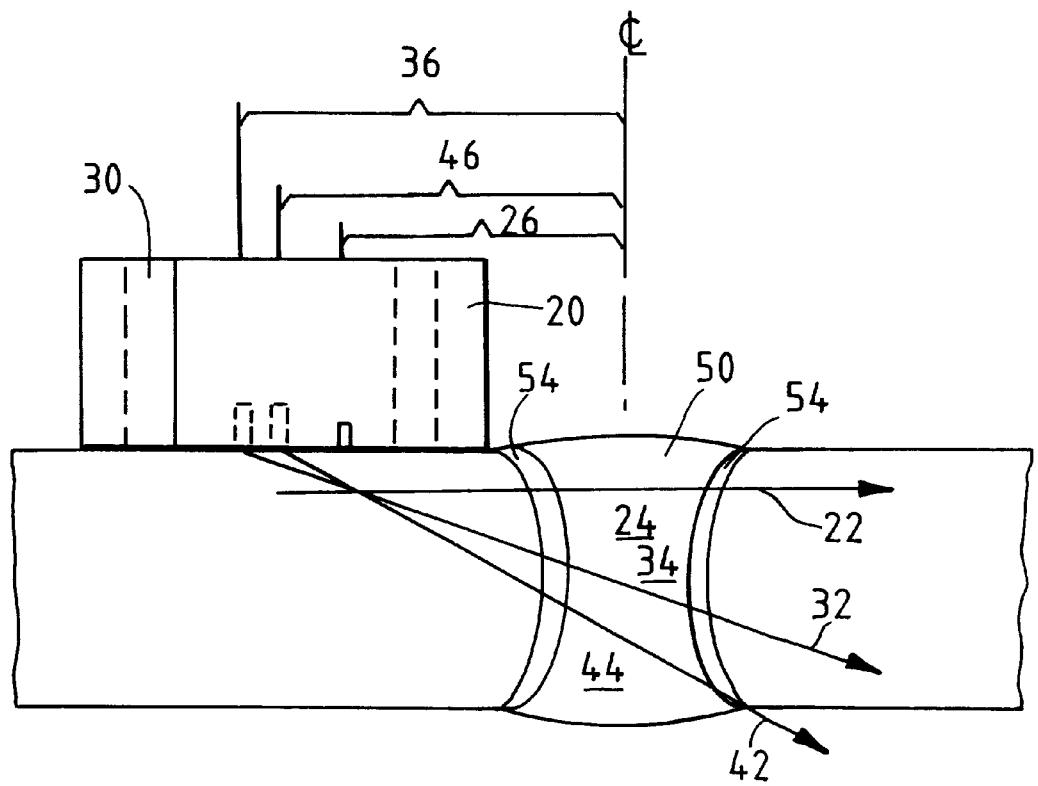
FIG. 3 is an enlarged view of FIG. 2.

As seen in FIG. 3 the creep wave transducer 20 is configured to emit a sound along an upper sound path 22 to an upper portion 24 of the weld metal 50 and heat-affected zones 54. In the illustrated embodiment of the invention, the creep wave transducer has a 40×40 mm housing, a 33 mm standoff distance 26 from the centerline of the weld to be inspected, and a frequency of 2 to 4 MHz. Other transducers could also be used to inspect the upper portion of the weld metal and heat-affected zones, but use of a creep wave transducer is preferred.

The intermediate-zone transducer 30 is configured to emit a sound along an intermediate sound path 32 to an intermediate portion 34 of the weld metal 50 and heat-affected zones 54. In the illustrated embodiment of the invention, the intermediate-zone transducer is a dual-element, 70° longitudinal wave (L-wave) transducer that has a 40×40 mm housing, a 44 mm standoff distance 36 from the centerline of the weld to be inspected, and a frequency of 2 to 4 MHz. Other transducers could also be used to inspect the intermediate portion.

The lower-zone transducer 40 (not seen) is configured to emit a sound along a lower sound path 42 to a lower portion 44 of the weld metal 50 and heat-affected zones 54. In the illustrated embodiment of the invention, the lower-zone transducer is a dual-element, 60° L-wave transducer that has a 40×40 mm housing, a 40 mm standoff distance 46 from the centerline of the weld to be inspected, and a frequency of 2 to 4 MHz. Other transducers could also be used to inspect the lower portion.

As seen in FIG. 1, the illustrated carriage also includes a position encoder 60 that monitors the position of the carriage as it travels along the length of the weld seam. The transducers 20, 30, and 40 are connected to a computer 68 that is programed with one set of gain (sensitivity) and gate settings for obtaining and analyzing direct reflections of the sound transmitted by the transducers, and a second set of gain and gate settings for obtaining and analyzing any indirect reflections of the sound transmitted by the intermediate-zone transducer 30 along the intermediate sound path 32. (The path taken by such indirect reflections is discussed below.) In the illustrated embodiment of the invention, the intermediate-zone transducer has gate settings for a 35 mm start and 25 mm length for obtaining and analyzing direct reflections of the sound from the intermediate transducer, and gate settings for a 56 mm start and 20 mm length for obtaining and analyzing indirect reflections of that sound.

A carriage like the one seen in FIGS. 1–3 can be configured by a relatively simple, innovative method.

Figure 4:
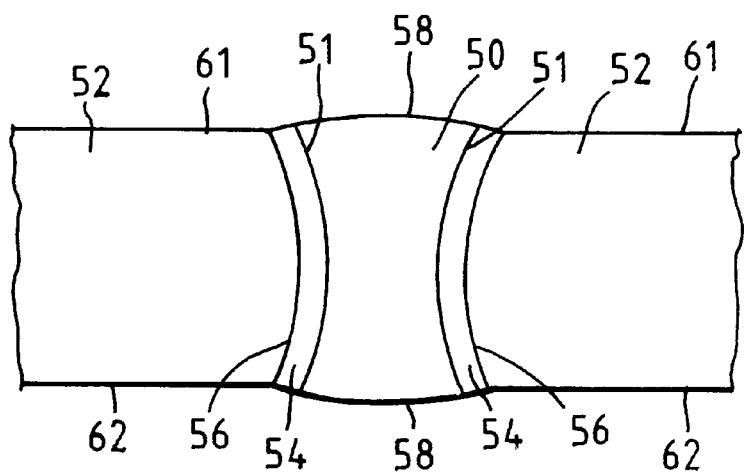
FIGS. 4–8 are embodiments of a schematic used in connection with method of the present invention.

First, the thickness and joint details of the weld seam to be inspected are evaluated. A schematic of a section through the weld is then prepared. An example of such a schematic is seen in FIG. 4. The illustrated section is perpendicular to the centerline axis of the weld. As illustrated, the schematic includes representations of the fusion lines 51 between the weld metal 50 and the plates 52, the boundaries 56 of the heat-affected zones 54 in the plates, surface profiles 58 of the weld metal 50, and upper and lower surfaces 61, 62 of the plates 52. The representations need only be approximations of the actual features found in the weld metal and plates to be inspected, but it is preferred that the approximations be relatively accurate.

Figure 5A:
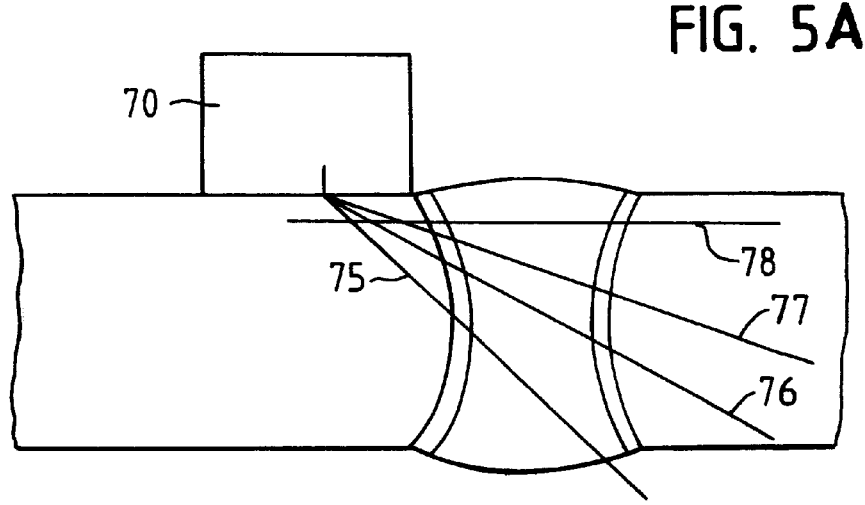
Figure 5B:
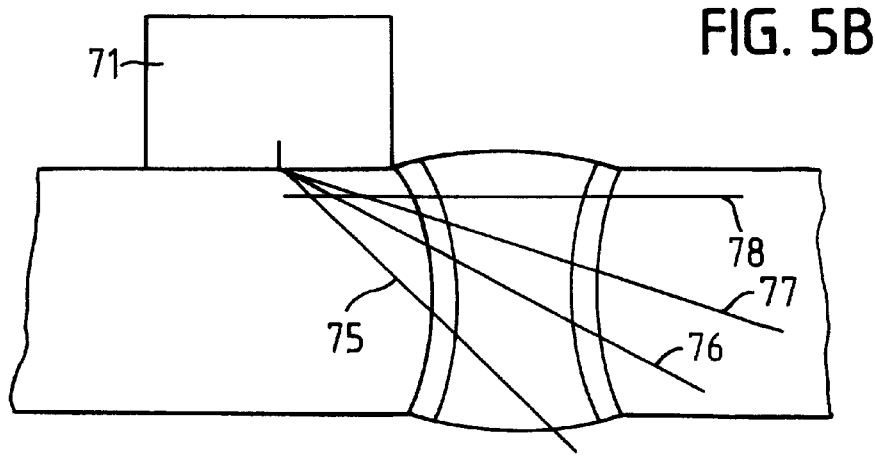
Figure 5C:
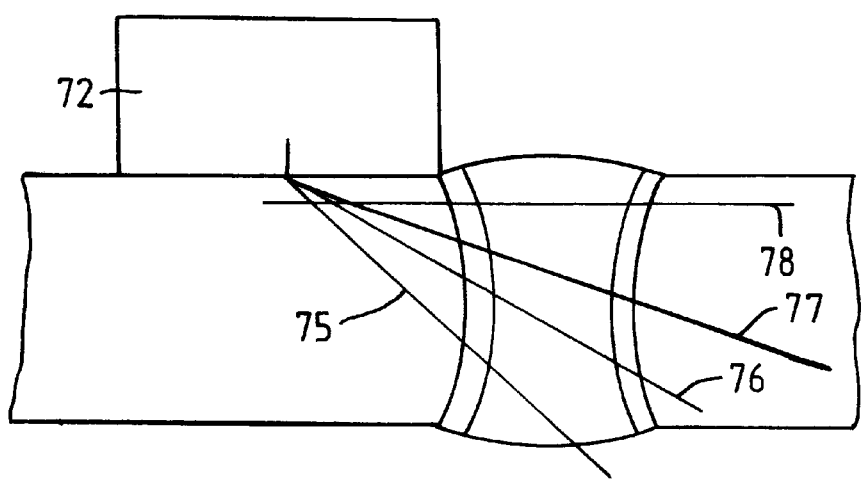

Transducer positions and potential transducer sound paths for the transducer positions are then laid-out on the schematic. In FIG. 5, three separate copies of the schematic are used to show transducer positions and sound paths for three different standard transducers 70, 71, and 72 commonly available in the marketplace. For each transducer, a 45° sound path 75, a 60° sound path 76, a 70° sound path 77, and a creep-wave sound path 78 are shown.

Figure 6A:
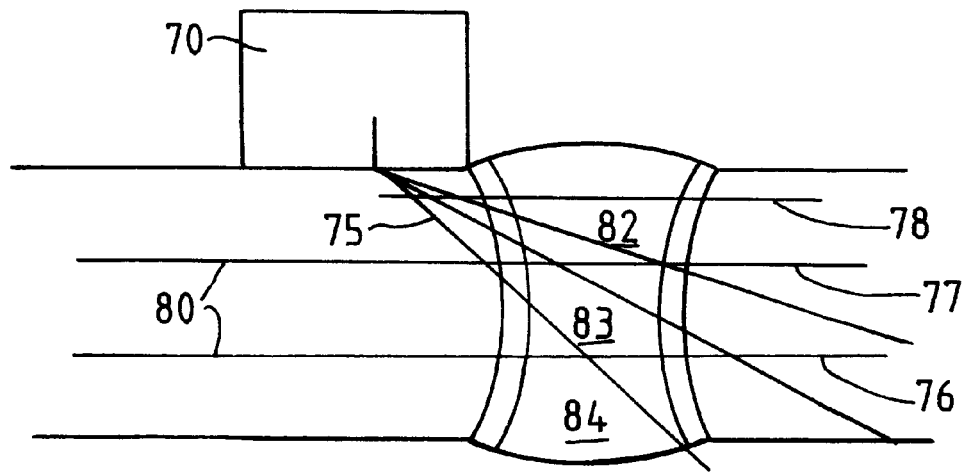
Figure 6B:
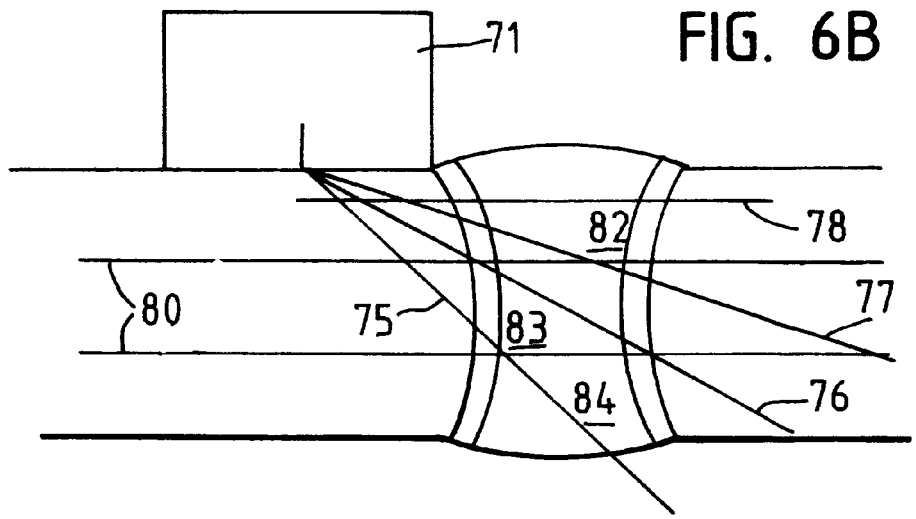
Figure 6C:
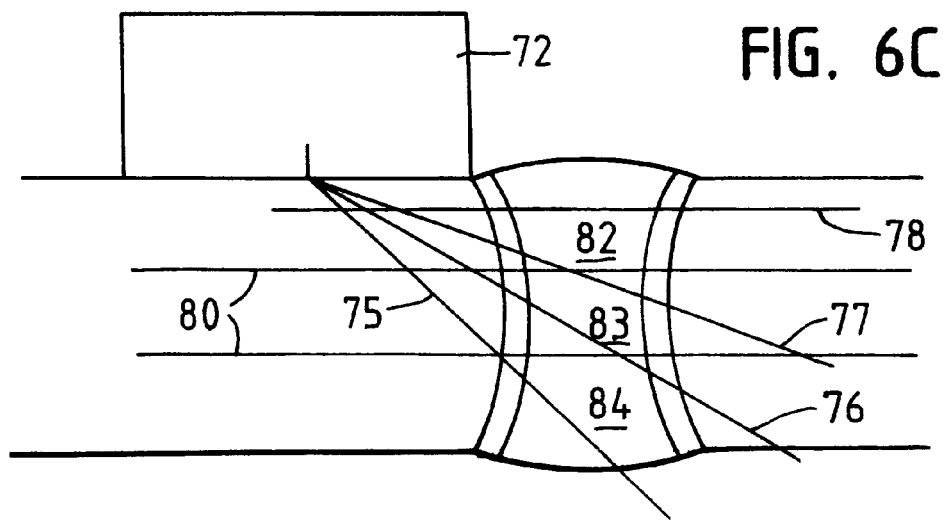

Next the weld metal 50 and heat-affected zones 54 on the schematic are divided into at least two inspection zones. In FIG. 6, horizontal dividing lines 80 have been added to the schematics of FIG. 5 to divide the weld metal and heat-affected zones of the schematics into three zones of equal width: an upper inspection zone 82, an intermediate inspection zone 83, and a lower inspection zone 84. Although preferred, the dividing lines need not be perfectly horizontal, or even straight, and the zones need not be of equal width. With transducers in common use today, it is preferred that each zone represents a maximum of approximately 8–10 mm of thickness of the actual weld metal and heat-affected zones, so for plates having a thickness of less than about 16 mm, the schematic of the weld metal and heat-affected zones need only be divided into two inspection zones, and for plates having a thickness of more than about 32 mm, the schematic would be divided into at least four inspection zones.

Figure 7A:
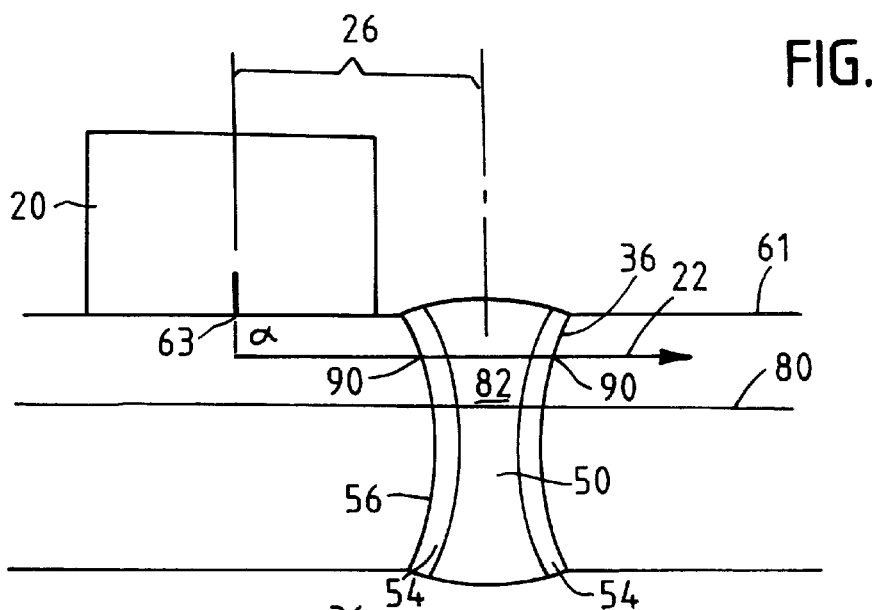
Figure 7B:
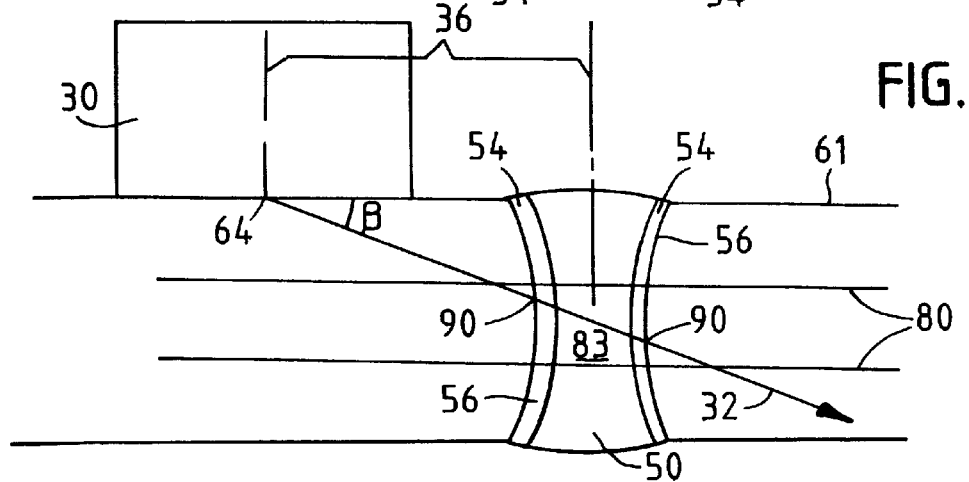
Figure 7C:
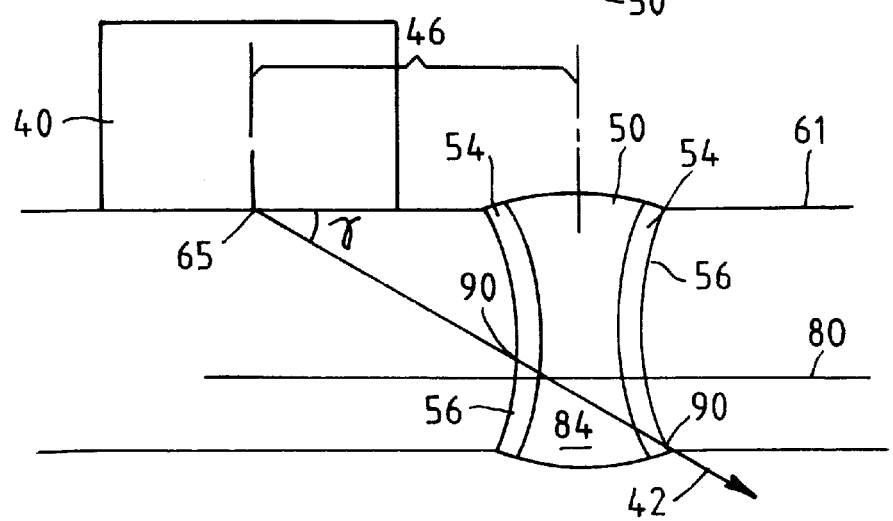

Based on the schematic, a transducer is then selected to inspect each inspection zone. In selecting a transducer, a housing size and sound path angle are each specified. Review of FIG. 6 could lead, for example, to the selection of a 40×40 mm creep-wave transducer for the upper inspection zone 82, a 40×40 mm, 70° L-wave transducer for the intermediate inspection zone 83, and a 40×40 mm, 60° L-wave transducer for the lower inspection zone 84. It is generally preferable to use a creep-wave transducer for the upper inspection zone. As seen in FIG. 7, sound paths 22, 32, and 42 are drawn at transducer sound path angles , β, and γ so that they pass through the respective inspection zones. The points where the sound paths intersect the top surface 61 of the plates define transducer positions 63, 64, and 65. It is preferred, but not essential, that the drawn sound path for each zone will cross the boundary 56 of each of the heat-affected zones 54 within that inspection zone. The drawn sound path 42 for the lower inspection zone 84 does not cross the boundary 56 for the heat-affected zone within the lower inspection zone. However, the drawn line only represents the centerline of the sound path. Because the sound from the transducer actually covers a broader area, it is sufficient that the drawn lines are in close proximity. Preferably, transducer housing sizes are selected so that the transducers will not come into contact with the weld metal 50 as the weld is inspected. Setting housing sizes and standoff distances 26, 36, 46 in this way obviates the need to smooth the weld seam before inspection.

Next, a focal spot distance is determined for each transducer. First, a minimum and maximum sound path distance is measured from the transducer positions 63, 64, and 65 where the sound paths intersect the top surface of the plates to inspection limits 90 for each transducer's inspection zone. As illustrated, the inspection limits are located where the sound path from that transducer position intersects the boundaries of the heat-affected zones 54. Alternatively, the inspection limits might be placed at the points where the sound path enters the inspection zone, or at some intermediate or similar point. In the illustrated embodiment of the invention, the minimum and maximum sound path distances for the creep-wave transducer 20, the intermediate-zone transducer 30, and the lower-zone transducer 40 are 16 mm and 47 mm, 35 mm and 60 mm, and 36 mm and 60 mm, respectively.

For each transducer, a focal spot distance is then selected that will provide adequate sensitivity at both the maximum sound path distance and the nimimum sound path distance for that transducer. Preferably, assuring adequate sensitivity is done by selecting a focal spot distance that is at least one-half of the maximum sound path distance, and no more than twice the minimum sound path distance. In the illustrated embodiment of the invention, the focal spots for the creep-wave transducer, the intermediate-zone transducer, and the lower-zone transducer are between 24 mm and 32 mm, 30 mm and 70 mm, and 30 mm and 72 mm, respectively.

Standoff distances for each transducer may be measured directly from the schematic. In FIG. 7, standoff distances 26, 36, and 46 are measured from the centerline of the weld metal 50 to the transducer positions 63, 64, and 65. Other reference distances could also be used. The standoff distances for the illustrated creep-wave transducer 20, the intermediate-zone transducer 30, and the lower-zone transducer 40 are 33 mm, 44 mm, and 40 mm, respectively.

Gate settings are then selected for each transducer. For directly-reflected signals, it is preferable to use the measured minimum sound path distances for the start gate settings for each transducer, and to select length gate settings that are equal to the difference between the measured minimum and maximum sound path distances. In the illustrated embodiment, this results in start gate settings and length gate settings for directly-reflected signals from the creep-wave transducer, the intermediate-zone transducer, and the lower-zone transducer of 16 mm and 31 mm; 35 mm and 25 mm; and 36 mm and 24 mm, respectively.

Figure 8:
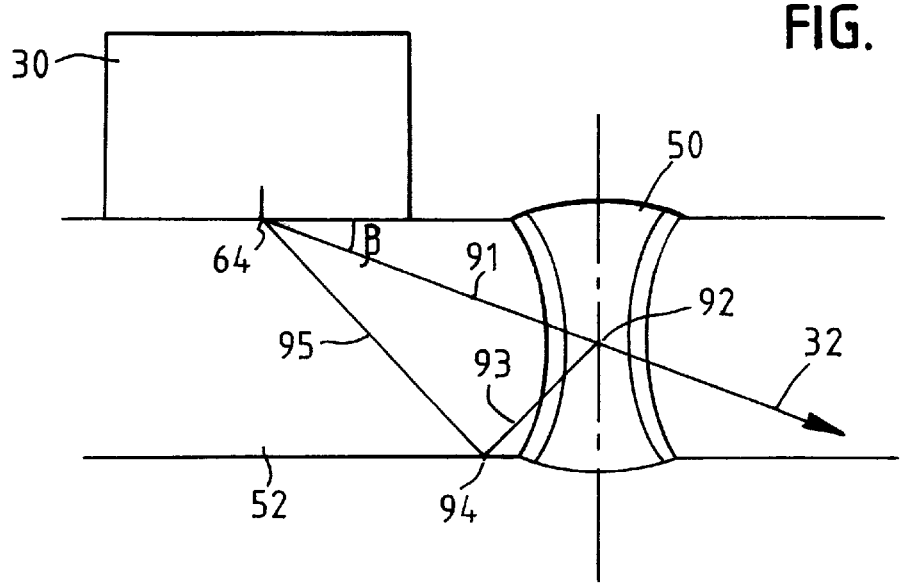

Gate settings may also be set for indirectly-reflected signals from one or more of the transducers. In FIG. 8, a "round-trip" sound path distance is determined using the distances of three legs: a first leg 91 from the transducer position 64 along the sound path 32 to a first reflecting position 92 at the centerline of the weld metal 50, a second leg 93 from the first reflecting position to a mode-converting position 94 on the lower surface of one of the plates 52, and a third leg 95 from the mode-converting position back to the transducer position. In the illustration, the third leg has been drawn at an angle of approximately 32°, because the illustrated 70° L-wave transducer is particularly sensitive to shear waves reaching it at that angle. Other transducers are most sensitive to shear waves at other angles, and it may be preferred to draw the legs at different angles for different transducers. Similarly, the first reflecting position could be set at other points along the first leg. Preferably, however, it falls within the weld metal or at least one of the heat-affected zones. When measuring the round trip sound path distance, the length of the third leg should be multiplied by an appropriate multiplier to account for the different speed of travel of the mode-converted shear-wave leg 95. In FIG. 8, the actual distances of the legs 91, 93 and 95 are 40 mm, 26 mm, and 36 mm, respectively. Multiplying the length of the third leg by 1.8 provides a total round-trip effective distance of 131 mm. The round-trip effective distance is halved to provide an effective direct distance of 66 mm for indirectly-reflected signals.

It is preferable to set the start gate setting for obtaining such indirectly-reflected signals by reducing this round-trip effective distance by approximately 10 mm (or approximately half the width of the weld metal and heat-affected zones) to effectively cover the area of interest for the illustrated embodiment. In the illustrated embodiment, this results in a start gate setting of 56 mm for an indirectly-reflected sound from the transducer. The length gate setting for the indirectly-reflected signal is preferably derived by doubling the 10 mm distance. Consequently, in FIG. 8, the length gate setting for an indirectly-reflected signal from the transducer is 20 mm.

Figure 9:
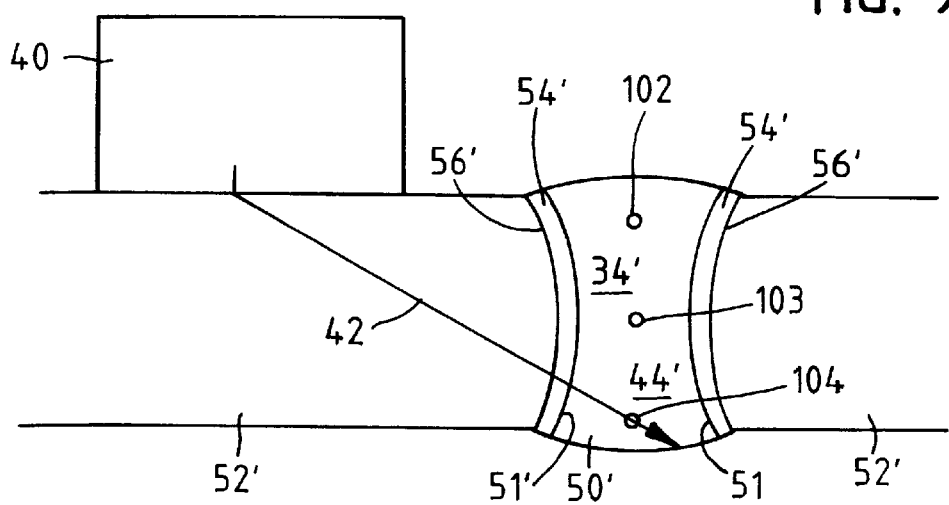
FIGS. 9 and 10 are cross-sectional views showing test plates for use in connection with the present invention.

Suitable gain settings for each transducer can be determined by using test plates, such as those seen in FIG. 9. The test plates 52' that are seen in FIG. 9 are made from materials that are similar to the materials in the weld seam to be screened and have a geometry that is similar to the geometry of the weld seam to be screened (that is, the test plates are similar in thickness and material to the plates in the weld to be screened, have similar test weld metal 50', and have fusion lines 51' and boundaries 56' of the heat-affect zones 54' that are similar in contour to the fusion lines and boundaries in the weld to be screened). It is also preferred that the test plates include machined reference reflectors in the test weld. In FIG. 9, the reflectors include side-drilled holes 102, 103, and 104. A sample of each selected transducer is placed at an appropriate distance from the test weld metal so that its sound path is directed toward the side-drilled hole in its respective inspection zone. In FIG. 9, the lower zone transducer 40 is positioned so that its sound path 42 is directed toward the side-drilled hole 104 in the lower inspection zone 44'. With an appropriate gain setting, this transducer should detect not only the side-drilled hole 104 in the lower inspection zone, but also the side-drilled hole 103 in the intermediate inspection zone 34'. Preferably, there is less than a 6dB drop in response between the signal from the side-drilled hole in the lower zone and the side-drilled hole in the intermediate zone. This drop criteria has been found to provide adequate width-of field for many applications. Preferably, each transducer gain setting is set so that the signal that is obtained on the computer 68 reaches 80% of the full-screen height for all transducer paths. The same gain setting minus 6dB can be generally used for the gain setting for indirectly-reflected signals.

After gain settings have been established for all transducers, the carriage seen in FIG. 1 can be assembled. On the carriage, the selected transducers 20, 30, and 40 are mounted at their respective standoff distances 26, 36, and 46, as seen in FIG. 1. As also seen in that figure, it is preferable to include matching transducers 20', 30', and 40' for each transducer. Matching transducers are preferably mounted on the opposite side of the carriage, to improve the reliability of the screening results. Appropriate software is set up to collect, analyze, and display data received from the transducers as a weld is inspected. In setting up the software, it is useful to connect one or more of the transducers on multiple channels, one channel with gain and gate settings for obtaining and analyzing directly-reflected sounds from the transducer and the other channel with gain and gate settings for obtaining and analyzing indirectly-reflected sounds from the transducer.

Figure 10:
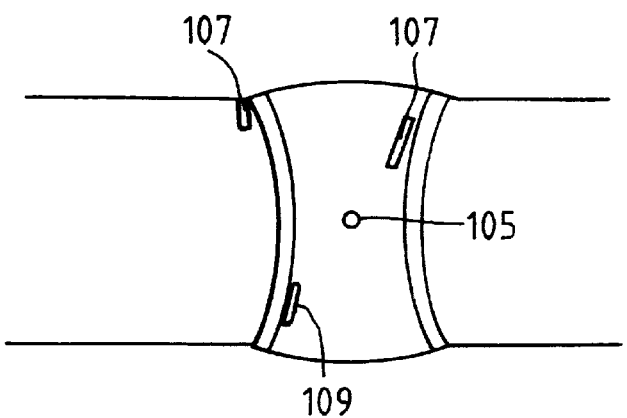

To confirm the reliability of the carriage and the set-up of the software, it is useful to test the carriage on an additional test weld seam, such as the one seen in FIG. 10. Again, the test weld seam should be made from materials that are similar to the materials in the weld seam to be screened, and should have a geometry that is similar to the geometry of the weld seam to be screened. It should also have artificial flaws, such as side-drilled holes 105, EDM notches 107, or welder-manipulated flaws 109.

In the field, all signals exceeding a threshold level should be evaluated against established acceptance criteria, or further evaluated by manual screening. Preferably, the threshold is set at 60% of the full screen height of the display.

What is claimed is:

1. A method for configuring an array of transducers in an ultrasonic test apparatus for screening for flaws in the volume of a weld seam that is made of austenitic material and has a pair of fusion lines at which the weld metal joins to a pair of plates, the method comprising the steps of:

(a) creating a schematic of a section through the weld that is perpendicular to the centerline axis of the weld, the schematic including representations of the fusion lines, boundaries of heat-affected zones in the plates, surface profiles of the weld metal, and upper and lower surfaces of the plates;

(b) laying-out on the schematic transducer positions and at least one transducer sound path;

(c) dividing the schematic of the weld into at least two inspection zones;

(d) selecting a transducer size and a sound path angle for each inspection zone;

(e) measuring a maximum sound path distance and a minimum sound path distance from each transducer position to inspection limits for that transducer's respective inspection zone;

(f) selecting a focal spot distance for each transducer that provides adequate sensitivity at both the maximum sound path distance and the minimum sound path distance;

(g) determining a transducer standoff distance for each transducer;

(h) determining gate settings for each transducer;

(i) providing test plates that are made from materials that are similar to the materials in the weld seam to be screened, have a geometry that is similar to the geometry of the weld seam to be screened, and have machined reference reflectors in the weld metal;

(j) using the test plates to determine a transducer gain setting for each transducer;

(k) using the test plates to confirm adequate width-of-field for each transducer;

(l) configuring a carriage capable of moving along the length of the weld seam by mounting the transducers at the standoff distances;

(m) providing test weld seams that are made from materials that are similar to the materials in the weld seam to be screened, have a geometry that is similar to the geometry of the weld seam to be screened, and have artificial flaws; and (n) using the carriage to inspect the test weld seams.

2. The method of claim 1 in which the inspection zones are of equal width.

3. The method of claim 1 in which the plates are at least about 16 mm thick, and an intermediate inspection zone is laid out on the schematic of the weld.

4. The method of claim 1, in which the gate settings are for receiving directly-reflected sound, and additional gate settings are determined for receiving indirectly-reflected sound with of the transducers.

5. The method of claim 1, in which the transducer gain settings are for receiving directly-reflected sound, and an additional gain setting is determined for receiving indirectly-reflected sound with one of the transducers.

6. The method of claim 1, in which the transducer used for inspecting the upper inspection zone is a creep-wave transducer.

7. The method of claim 1 wherein at least one of the transducers is a longitudinal wave transducer that has a frequency of 2 to 4 MHz.

8. A method of claim 1, in which:

(a) the inspections zones include an upper portion of the weld metal and the heat-affected zone, and a lower portion of the weld metal and the heat-affected zone;

(a) a creep wave transducer is selected to inspect the upper portion of the weld metal and heat-affected zones;

(b) a second transducer is selected to inspect a lower portion of the weld metal and heat-affected zones;

(c) two sets of gate settings are selected for the second transducer, one set for indirectly-reflected sound and the other set for directly-reflected sound from the same transducer;

(d) two transducer gain settings are selected for the second transducer, one gain setting for the indirectly-reflected sound and the other gain setting for the directly-reflected sound; and (e) a processor is programed to analyze signals from the second transducer as signals from two transducers.

9. The method of claim 8, in which the gain setting for the directly-reflected sound is at least twice as sensitive as die gain setting for the indirectly-reflected sound.

10. The method of claim 8, in which at least one of the transducers is a longitudinal wave transducer that has a frequency of 2 to 4 MHz.

11. An apparatus for screening for flaws in the volume of a weld seam that is made of austenitic material and has a pair of fusion lines at which the weld metal joins to a pair of places, the apparatus having been configured in accordance with the method of claim 1.

12. An apparatus as recited in claim 11, comprising:

(a) a creep-wave transducer configured to transmit a first sound to an upper inspection zone;

(b) a second transducer configured to transmit a second sound to a lower inspection zone; and (d) a processor programmed with both a first set of gain and gate settings for obtaining and analyzing direct reflections of the second sound, and a second set of gain and gate settings for obtaining and analyzing indirect reflections of the second sound.

13. The apparatus of claim 11, in which at least one of the transducers is a longitudinal-wave transducer that has a frequency of 2 to 4 MHz.

14. The apparatus of claim 11 and further comprising a position-encoder.

15. The apparatus of claim 11, in which each transducer has a matching transducer mounted on the opposite side of the carriage.

16. A method for screening for flaws in the volume of a weld seam that is made of austenitic material and has a pair of fusion lines at which the weld metal joins to a pair of plates, the method comprising the steps of:

(a) configuring a carriage in accordance with the method of claim 1; and (b) using the carriage to screen for flaws in the volume of the weld seam.

17. A method as recited in claim 16 in which:

the carriage is provided with a creep-wave transducer and a second transducer;

the carriage is connected to a processor having first and second gain and gate settings for the second transducer;

a first sound from the creep-wave transducer is transmitted to an upper portion of the weld metal and heat-affected zones, and a second sound from the second transducer is transmitted to a lower portion of the weld metal and heat-affected zones; and the first set of gain and gate settings is used to obtain and analyze direct reflections of the second sound, and the second gain and gate settings is used to obtain and analyze indirect reflections of the second sound.

* * * * *

UNITED STATES PATENT AND TRADEMARK OFFICE
CERTIFICATE OF CORRECTION

PATENT NO.    : 6,405,596 B1
DATED         : June 18, 2002
INVENTOR(S)   : Ronald W. Kruzic It is certified that error appears in the above-identified patent and that said Letters Patent is hereby corrected as shown below:

Column 7,
Line 51, add the word -- one -- before "of the transducers"

Column 8,
Line 15, remove "die" and replace with -- the --

Signed and Sealed this

Seventh Day of January, 2003

JAMES E. ROGAN
*Director of the United States Patent and Trademark Office*